United States Patent
Magidson

[11] Patent Number: 5,829,062
[45] Date of Patent: Nov. 3, 1998

[54] HEADBAND WITH DUAL MATERIAL CONSTRUCTION FOR SUPPORTING EAR PROTECTORS

[75] Inventor: Mark Magidson, Los Angeles, Calif.

[73] Assignee: Moldex-Metric, Inc., Culver City, Calif.

[21] Appl. No.: 734,201

[22] Filed: Oct. 21, 1996

[51] Int. Cl.⁶ ........................................ A61F 11/06
[52] U.S. Cl. ................ 2/209; 2/171; 2/DIG. 11; 128/867
[58] Field of Search ................ 2/209, 455, 171, 2/DIG. 11; 128/864, 866, 867, 868

[56] References Cited

U.S. PATENT DOCUMENTS 2,924,672  2/1960  Cagen .......................................... 2/209
3,167,619  1/1965  Palmaer ........................................ 2/209

*Primary Examiner*—Diana Biefeld
*Attorney, Agent, or Firm*—Charles H. Schwartz

[57] ABSTRACT

A headband ear protector apparatus including a pair of ear protectors and a resilient head band supporting, at opposite ends of the headband, the ear protectors. This forms a band which positions the ear protectors to lie by the opposite ears of a person. The headband is formed of a combination of hard and soft materials. The hard material is formed as a main support member for the ear protectors to extend between the ear protectors and provide resilience so the ear protectors will lie by the opposite ears of the person. The main support member includes at least one region having structure to receive the soft material to provide sound attenuation for reducing sound transmitted through the headband to the ear protectors.

14 Claims, 1 Drawing Sheet

HEADBAND WITH DUAL MATERIAL CONSTRUCTION FOR SUPPORTING EAR PROTECTORS

BACKGROUND OF THE INVENTION

The present invention relates to a headband ear protector which generally includes a headband supporting a pair of ear protectors. The headband presses the ear protectors around and partially into the outer end of the ear canal of a user. In particular, the present invention relates to a headband having a dual material construction to reduce sound transmission to the ear canal through the head-band.

Generally, there are a number of different types of ear protectors currently in use. One type is an earplug which is inserted fairly deeply into the ear canal. As an example, one type of such earplug is made of a slow recovery resilient foam material so that the earplug can be rolled down and inserted into the ear canal. There are times, however, when it is desired not to have an earplug inserted deeply into the ear canal.

Another type of ear protector apparatus includes a headband that presses a pair of ear protectors around and partially into the outer end of the ear canal. This type of structure avoids the necessity to insert an earplug deeply into the ear canal and is generally defined as a semi-aural headband hearing protector.

Typically, the headband is made of a hard plastic or metal to provide for sufficient resiliency to press the ear protectors to lie against and partially into the ear canal so as to produce the desired sound attenuation. One problem with this type of headband is that there is an annoying phenomena of sound transmitting through the band into the user's ear canal. This occurs most commonly when the band rubs against the user's clothing, skin whiskers or any other object.

Independent hearing protector evaluation laboratories evaluates these protectors on a regular basis and the subjects routinely complain of the band-generated noise, usually from the band touching clothing. The sound is generated in the ear when the band vibrations are transmitted to the ear protectors. The vibrations generate sound pressure in the small volume of air between the tip of the ear protector and the tympanic membrane. Because the air volume is small and the membrane is extremely sensitive to variation in pressure, these ear protector vibrations are perceived as relatively loud sounds that usually cover a wide frequency range. The broadband noise is generally considered annoying and potentially it can mask useful sounds, such as speech communication or important machine operating sounds. The development of a semi-aural hearing protector headband that decreased transmitted noise would be beneficial to wearers of this type of protection.

The bands are typically worn under the chin and the band can thereby contact a user's clothing, skin etc. in the course of moving the head to different positions. Even if the band is worn in other positions such as over or around the head, this can still create problems. If the band contacts any object, this produces the transmission of sound through the band into the user's ear canal.

SUMMARY OF THE INVENTION

The present invention reduces significantly the sound transmission through the headband into the user's ear canal. This is accomplished by constructing the headband of two types of material: a hard plastic and a soft plastic. As an example, the headband may have a main support member made of a hard resilient plastic. The main support member provides the resiliency so that the ear protectors can lie by and partially into the ears of the user. The hard plastic main support member includes at least one region having a structure to receive a soft plastic material. The soft plastic dampens vibrations to provide sound attenuation to reduce sound transmitted through the headband to the ear protectors.

The headband may be constructed using different methods of manufacture. These methods include co-injection molding of the type currently used to produce products such as toothbrush handles which have co-injected plastics. Other methods include molding the hard plastic main support member with the region formed as a cavity and then the soft plastic material is inserted into the cavity formed in the hard plastic support member. In either event, the headband with the dual molded material construction has the advantage of reducing the amount of sound transmitted through the band when compared with a headband that is formed only with the typical hard material.

Two semi-aural hearing protector headbands manufactured by applicant were evaluated by an independent laboratory. Both headbands had the same physical configuration and one headband was of standard construction of a single plastic material and the other headband was of dual-molded band construction in accordance with the teachings of the present invention. The goal of the evaluation was to determine if either of the two bands was less susceptible to vibration transmission. To measure the vibration characteristics of the bands, the bands were fixed in a vise and stimulated with a rotating foam ball. One accelerometer was placed at the point of the stimulus and a second was placed at the end of the band where the ear protector would normally be located. This configuration provided the best measure of ear protector vibration that would occur as a result of a rubbing-type of physical contact with the band.

The cross-spectrum of the two accelerometers was used as a measure of susceptibility to vibration. In this case, the cross-spectrum is the frequency spectrum of the point of stimulus divided by the frequency spectrum of the tip of the band. The cross-spectrum is not dependent on the magnitude of the stimulus. This is critical in this experiment since it would be extremely difficult to precisely repeat the physical location of the bands in reference to the foam ball. In addition, the characteristics of the foam ball may have changed slightly during the test, as particles rub off or as the ball becomes slightly compressed. Again, the measurements were not effected by these changes since the cross-spectrum metric was used.

Examination of the cross-spectrum readings reveal that, in general, the dual-molded band is less susceptible to vibration in the 2000–5000 Hz range. Within this range, the dual-molded band is damped and less resonant than the standard band. These characteristics make the frequency response flatter, without the resonant peaks that are present in the transfer function of the standard band. In other frequency ranges, there is less difference between the two bands. The measurements indicated that the dual-molded band also appears to be vibrate somewhat less around 6000 Hz and the standard band tends to vibrate less around 7000 Hz.

A clearer understanding of the invention will be had with reference to the following description and drawings.

DETAILED DESCRIPTION OF THE PREFERRED EMBODIMENT

Figure 1:
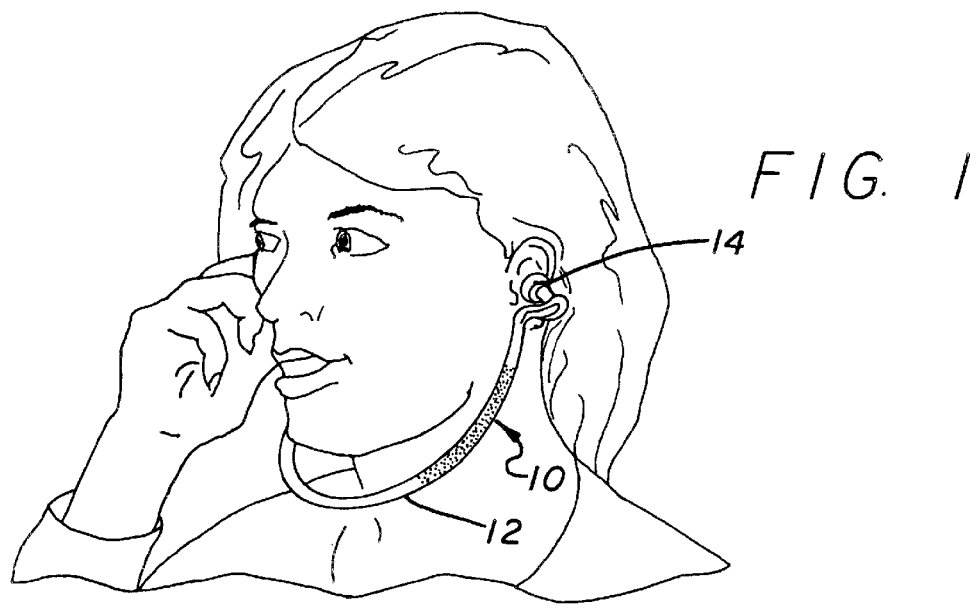
FIG. 1 illustrates a headband ear protector apparatus constructed in accordance with the teachings of the present invention and shown positioned under the chin of a user.
Figure 2:
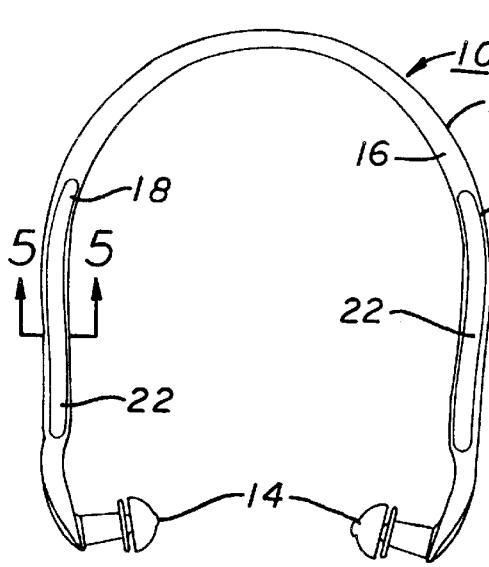
FIG. 2 is a back view of the headband ear protector.
Figure 3:
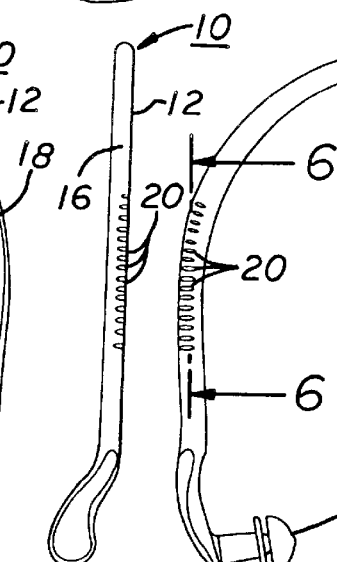
FIG. 3 is a side view of the headband ear protector.
Figure 4:
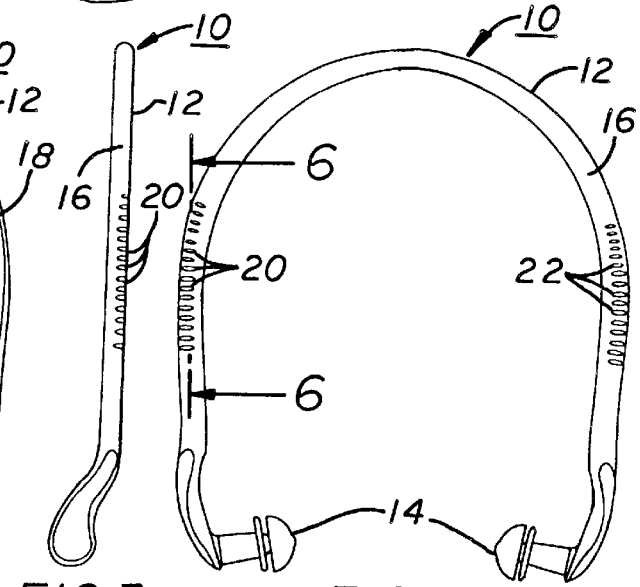
FIG. 4 is a front view of the ear band ear protector.
Figure 5:
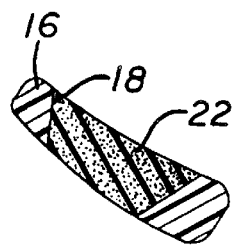
FIG. 5 is a cross-sectional view of the headband taken along lines 5—5 of FIG. 2.

In FIG. 1, a headband ear protector apparatus 10 of the present invention is shown and is formed by a headband 12 and ear protectors 14. The apparatus is shown worn under the chin of a user. If the headband portion 12 rubs against the user's clothing or skin or contacts a solid object, there can be sound transmission through the headband 12 to the ear protectors 14 and then into the user's ear canal. The sound transmission can be very annoying to the user and could even limit the use for sound protection purposes.

Typically, the ear protectors 14 have a shape to provide for a partial insertion of the ear protector 14 into the outer end of the ear canal as well as covering the outside entrance to the ear canal. This partial insertion of the ear protector 14 can heighten the transmission of sound through the headband 12 into the ear canal. The ear protectors 14 are typically made of a soft plastic material such as urethane foam, PVC or PVC foam.

The present invention significantly reduces the amount of sound transmitted through the headband by constructing the headband out of dual materials. Specifically, a hard resilient plastic material forms a main support member to maintain the ear protectors 14 positioned against the ear canal. A soft plastic material reduces the transmission of sound through the headband. As can be seen in the drawings, and specifically FIGS. 2–6, the headband 12 includes a main support member 16 constructed of a hard resilient plastic. For example, the member 16 may be polycarbonate or polypropylene as well as other hard polymers.

The main support member 16 includes at least one region having a structure to receive soft material. In the specific example shown in the drawings, the region is formed by cavities 18 positioned at opposite ends of the member 16. As can be seen in the drawings, each cavity extends substantially along the length of the main support member 16 along one side and with a series of smaller openings 20 extending from the cavity 18 through the main support member to the other side.

Figure 6:
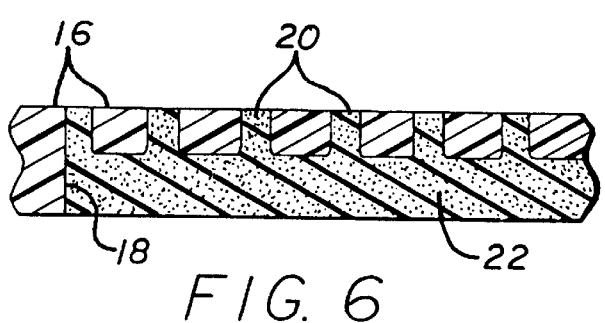
FIG. 6 is a cross-sectional view of the headband ear protector taken along lines 6—6 of FIG. 4.

As can be seen in FIG. 6 each cavity 18 with the extending openings 20 forms an elongated cavity within the support member 16 to receive a separate soft plastic insert material 22. The soft plastic material 22 fills each cavity 18 and extends through the smaller openings 20 to provide for a substantial amount of soft plastic material arranged longitudinally along the length of the headband 12 at the areas adjacent to the ear protectors 14. The soft flexible plastic material 22 may be material such as Monprene which is a trademark for a particular soft polymer sold by the QST, Incorporated. Another example of a soft plastic may be Kraton which is a similar polymer sold by the Shell Chemical Co. It is to be appreciated that other similar soft polymers may be used for the material 22.

The present invention therefore is directed to a headband ear protector apparatus and specifically to the headband portion which supports the ear protectors. The headband is formed of dual materials including a hard plastic main support member having at least one region having a structure to receive a soft plastic to provide for sound attenuation to reduce the sound transmitted through the headband to the ear protector. The headband may be constructed using one of a number of common methods. One method is a co-injection molding technique and this method is currently used to produce products such as toothbrushes. The handle of the toothbrush is constructed of a soft plastic coinjected into a hard plastic handle. Other techniques that may be used would be to actually mold the main hard support member first, again using injection molding techniques. After the main hard plastic member is molded then a soft plastic material may be injected into a cavity formed initially in the main support member.

It is also to be appreciated that the ear protectors 14 may take a variety of forms including that shown in the present application as well as forms which do not enter into the ear canal and would be generally referred to as an ear muff.

Although the invention has been described with reference to a particular embodiment, it is to be appreciated that various adaptations and modifications may be made and the invention is only to be limited by the appended claims.

I claim:

1. A headband ear protector apparatus including a pair of ear protectors, a resilient headband supporting, at opposite ends of the headband, the ear protectors to form a band which positions the ear protectors to lie by the opposite ears of a person, the headband formed of a combination of hard and soft materials and having the following structure, the hard material formed as a main support member for the ear protectors to extend between the ear protectors and provide resilience so the ear protectors will lie by the opposite ears of a person, the main support member including at least one region forming a depression to receive soft material, and the soft material received by the at least one region to provide sound attenuation for reducing sound transmitted through the headband to the ear protectors.

2. The headband ear protector apparatus of claim 1 wherein the at least one region extends completely through the main support member at at least one position so that the soft material also extends through the main support member.

3. The headband ear protector apparatus of claim 1 wherein two regions are formed at opposite ends of the main support member.

4. The headband ear protector apparatus of claim 1 wherein the at least one region is formed with a continuous depression extending along the length of the main support member.

5. The headband ear protector apparatus of claim 4 wherein a plurality of additional adjacent openings extend completely through the main support member from the continuous depression.

6. The headband of claim 1 wherein both the hard and soft materials are plastic.

7. The headband of claim 6 wherein the hard plastic may be from the following group of plastics, namely polycarbonate, polypropylene and similar hard polymers and the soft plastic may be from the following group of plastics, namely "Monprene" (trademark for soft polymer sold by QST Incorporated), "Kraton" (trademark for soft polymer sold by Shell Chemical Co.), and similar soft polymer.

8. A headband for supporting ear protectors at opposite ends of the headband to position the ear protectors to lie by the opposite ears of a user, including the headband formed of a combination of hard and soft materials and having the following structure, the hard material formed as a main support member for the ear protectors to extend between the ear protectors and provide resilience so the ear protectors can lie by the opposite ears of a person, the main support member including at least one region forming a depression to receive soft material, and the soft material received by the at least one region to provide sound attenuation for reducing sound transmitted through the headband to the ear protectors.

9. The headband of claim 8 wherein the at least one region extends completely through the main support member at at least one position so that the soft material also extends through the main support member.

10. The headband of claim 8 wherein two regions are formed at opposite ends of the main support member.

11. The headband of claim 8 wherein the at least one region is formed with a continuous depression extending along the length of the main support member.

12. The headband of claim 11 wherein a plurality of additional adjacent depressions extend completely through the main support member from the continuous depression.

13. The headband of claim 8 wherein both the hard and soft materials are plastic.

14. The headband of claim 13 wherein the hard plastic may be from the following group of plastics, namely polycarbonate, polypropylene and similar hard polymers and the soft plastic may be from the following group of plastics, namely "Monprene" (trademark for soft polymer sold by QST Incorporated), "Kraton" (trademark for soft polymer sold by Shell Chemical Co.), and similar soft polymer.

* * * * *